United States Patent [19]
Breckenridge et al.

[11] Patent Number: 5,382,730
[45] Date of Patent: Jan. 17, 1995

[54] COMBINED PARAFFIN ISOMERIZATION/RING OPENING PROCESS

[75] Inventors: Lloyd L. Breckenridge, Philadelphia, Pa.; Kenneth J. Del Rossi, Woodbury, N.J.; Albin Huss, Jr., Chadds Ford, Pa.; Clinton R. Kennedy, West Chester, Pa.; Garry W. Kirker, Washington Twp., Gloucester County, N.J.

[73] Assignee: Mobil Oil Corp., Fairfax, Va.

[21] Appl. No.: 90,357

[22] Filed: Jul. 12, 1993

Related U.S. Application Data

[63] Continuation-in-part of Ser. No. 783,014, Oct. 25, 1991, abandoned.

[51] Int. Cl.$^6$ .............................................. C07C 5/27
[52] U.S. Cl. .................... 585/310; 585/739; 585/752; 585/940; 208/60
[58] Field of Search .......... 585/739, 940, 752, 310; 208/60

[56] References Cited

U.S. PATENT DOCUMENTS

| | | | |
|---|---|---|---|
| 3,631,117 | 12/1971 | Kovack et al. | 260/666 |
| 3,847,792 | 4/1974 | Berger | 208/60 |
| 3,923,641 | 12/1975 | Morrison | 208/111 |
| 3,930,986 | 11/1976 | Berger | 208/60 |
| 4,146,462 | 3/1979 | Rustamov et al. | 208/46 |
| 4,162,212 | 7/1979 | Miller | 208/79 |
| 4,175,033 | 11/1979 | Hilfman | 208/143 |
| 4,232,181 | 11/1980 | Klovsky et al. | 585/739 |
| 4,647,368 | 3/1987 | McGuiness et al. | 208/60 |
| 4,676,887 | 6/1987 | Fischer et al. | 208/61 |
| 4,734,539 | 3/1988 | Lawlor et al. | 585/739 |
| 4,783,575 | 11/1988 | Schmidt et al. | 585/748 |
| 4,804,803 | 2/1989 | Schmidt et al. | 585/748 |
| 4,834,866 | 5/1989 | Schmidt | 208/65 |
| 4,911,823 | 3/1990 | Chen et al. | 208/67 |
| 4,926,000 | 5/1990 | Morrison | 585/476 |
| 4,929,799 | 5/1990 | Holcombe | 585/737 |
| 4,990,239 | 2/1991 | Derr et al. | 208/68 |
| 5,055,629 | 10/1991 | Gilson et al. | 585/739 |
| 5,082,988 | 10/1992 | Holtermann | 585/739 |
| 5,095,169 | 3/1992 | Skeels et al. | 585/739 |

FOREIGN PATENT DOCUMENTS

| | | |
|---|---|---|
| 0398416 | 11/1990 | European Pat. Off. |
| WO9100851 | 1/1991 | WIPO |
| WO9308145 | 4/1993 | WIPO |

*Primary Examiner*—Asok Pal
*Attorney, Agent, or Firm*—Alexander J. McKillop; Dennis P. Santini; Edward F. Kenehan, Jr.

[57] ABSTRACT

There is provided a process for ring opening of aromatics and cycloaliphatics, as well as isomerization of aliphatics. The feedstream to this process comprises hydrocarbons having 6 carbon atoms. The process involves the use of at least two reactors connected in series. The first reactor comprises a zeolite catalyst and is operated under conditions which particularly promote ring opening. The catalyst in this first reactor may comprise zeolite Beta and platinum. A downstream reactor is operated under conditions to promote isomerization of aliphatics. The catalyst in the second reactor may comprise alumina, platinum and a chloride component. Hydrogen in the effluent of the first reactor may be removed and recycled to the first reactor. Hydrogen required for the second reactor may be satisfied by hydrogen remaining dissolved in the effluent from the first reactor after hydrogen is recycled to the first reactor.

23 Claims, 4 Drawing Sheets

COMBINED PARAFFIN ISOMERIZATION/RING OPENING PROCESS

CROSS-REFERENCE TO RELATED APPLICATION

This application is a continuation-in-part of copending U.S. application Ser. No. 07/783,014, filed Oct. 25, 1991, now abandoned the entire disclosure of which is expressly incorporated herein by reference.

BACKGROUND

There is provided a process for ring opening of aromatics and cycloaliphatics, as well as isomerization of aliphatics. The feedstream to this process comprises $C_6$ cycloparaffins and/or benzene. The process involves the use of at least two reactors connected in series. The first reactor comprises a zeolite catalyst and is operated under conditions which particularly promote ring opening. A downstream reactor is operated under conditions to promote isomerization of aliphatics.

A unit process which is frequently encountered in petroleum refining is paraffin isomerization. Paraffin isomerization of linear (straight chain) paraffins produces branched chain paraffins. In such a process, as conventionally operated, low molecular weight $C_4$-$C_6$ paraffins are converted to iso-paraffins in the presence of an acidic catalyst such as aluminum chloride. Recently, $C_6+$, preferably $C_{10}+$ n-paraffins, have been isomerized, in the presence of large pore size zeolites to produce branched chain paraffins by skeletal rearrangement. The latter process can find application in dewaxing.

Isomerization is one of several reactions which occur in reforming of naphthas. Reforming of naphthas is undertaken to upgrade a low octane naphtha to a higher octane effluent. One of the octane enhancing reactions which occurs during reforming is the isomerization of n-paraffins to isoparaffins. Under the process conditions of reforming, other reactions which occur are aromatization (or dehydrocyclization), and dehydrogenation, with some cracking.

Paraffin isomerization catalysts may also be employed as ring opening catalysts for removal of aromatics and aromatic precursors from reformer feedstocks. For example, cyclohexane, a precursor to benzene, may be rearranged over commercial paraffin isomerization catalysts to a mixture of branched paraffins. Branched paraffins are only partly aromatized in reforming whereas cyclohexane is almost completely converted to benzene. Application of paraffin isomerization catalysts for ring opening aromatics and aromatic precursors will no doubt become more important as environmental regulations limiting aromatics in gasoline become more stringent.

SUMMARY

There is provided a process for ring opening and isomerization of hydrocarbons, said process comprising the steps of:

(a) charging hydrocarbons comprising $C_6$ cyclic hydrocarbons along with hydrogen to a first reaction zone, wherein said hydrocarbons and hydrogen are contacted with a catalyst comprising a zeolite and a hydrogenation component under conditions sufficient to saturate benzene and open cyclic hydrocarbons contained in said hydrocarbons; and (b) charging the hydrocarbon product from said first reaction zone along with hydrogen to a second reaction zone, wherein hydrocarbons and hydrogen are contacted with an isomerization catalyst under conditions sufficient to isomerize paraffins.

There is also provided a process for ring opening and isomerization of hydrocarbons, said process comprising the steps of:

(a) passing hydrocarbons comprising $C_6$ cyclic hydrocarbons and a hydrocarbon recycle stream to a fractionation zone;

(b) withdrawing a sidecut comprising $C_6$ hydrocarbons and a majority of the $C_6$ cyclic hydrocarbons entering said fractionation zone;

(c) charging said sidecut along with hydrogen to a first reaction zone, wherein said sidecut and hydrogen are contacted with a catalyst comprising a zeolite and a hydrogenation component under conditions sufficient to saturate benzene and open cyclic hydrocarbons contained in the sidecut;

(d) charging the hydrocarbon product from said first reaction zone along with hydrogen to a second reaction zone, wherein hydrocarbons and hydrogen are contacted with an isomerization catalyst under conditions sufficient to isomerize paraffins;

(e) recovering an effluent from said second reaction zone and returning said effluent to said fractionation zone as said hydrocarbon recycle stream;

(f) recovering a second stream from said fractionation zone comprising $C_7$ hydrocarbons; and (g) recovering a third stream from said fractionation zone comprising 2,2-dimethylbutane and lower boiling hydrocarbons.

There is also provided a process for ring opening and isomerization of hydrocarbons, said process comprising the steps of:

(a) passing hydrocarbons comprising $C_6$ cyclic hydrocarbons and a hydrocarbon recycle stream to a fractionation zone;

(b) withdrawing a sidecut comprising $C_6$ hydrocarbons and a majority of the $C_6$ cyclic hydrocarbons entering said fractionation zone;

(c) charging said sidecut along with hydrogen to a first reaction zone, wherein said sidecut and hydrogen are contacted with a catalyst comprising a zeolite and a hydrogenation component under conditions sufficient to saturate benzene and open cyclic hydrocarbons contained in the sidecut;

(d) removing hydrogen from the effluent of the first reaction zone under conditions so that the effluent has a hydrogen to hydrocarbon mole ratio of less than 0.05;

(e) recycling hydrogen removed in accordance with step (d) to said first reaction zone;

(f) charging the effluent from said first reaction zone having a hydrogen to hydrocarbon mole ratio of less than 0.05 to a second reaction zone, wherein hydrocarbons and hydrogen are contacted with an isomerization catalyst under conditions sufficient to isomerize paraffins;

(g) recovering an effluent from the second reaction zone and returning said effluent from the second reaction zone to said fractionation zone as said hydrocarbon recycle stream;

(h) recovering a second stream from said fractionation zone comprising $C_7$ hydrocarbons; and (i) recovering a third stream from said fractionation zone comprising 2,2-dimethylbutane and lower boiling hydrocarbons.

EMBODIMENTS

Figure 1:
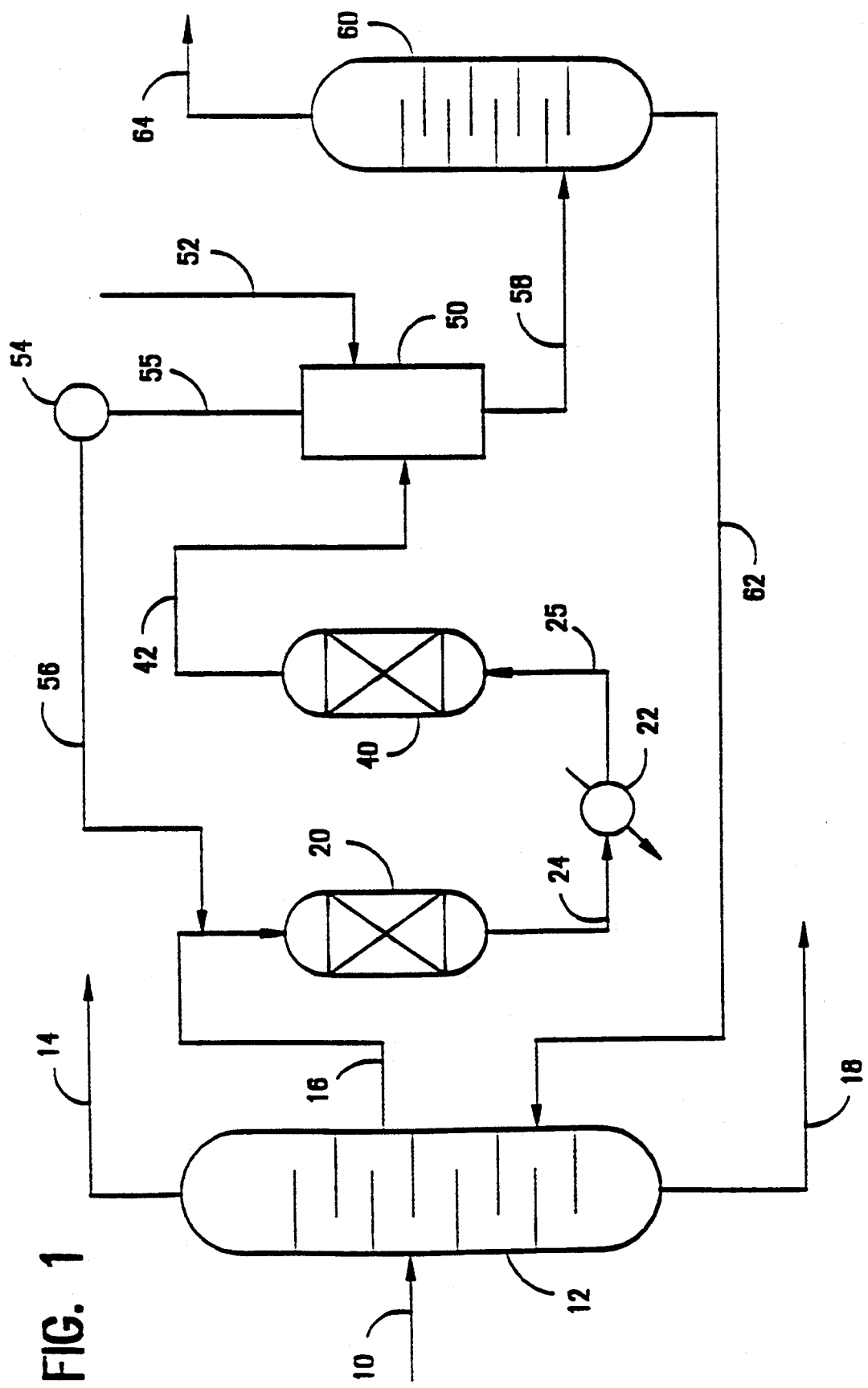
FIGS. 1 and 2 provide schematic representations of embodiments of the present process.

The catalytic ring opening/isomerization process described herein is operated to ring open $C_6$ cyclic hydrocarbons and isomerize the acyclic products together with n-paraffins and mono-methyl branched paraffins to produce a high octane stream.

In the present ring opening/isomerization process n-paraffinic and mono-methyl branched paraffinic components are isomerized to higher branched paraffins which are generally better octane boosters. By way of illustration, the significance of these reactions can be gleaned from a review of the following table of Octane Numbers of Pure Hydrocarbons from P. H. Emmett, ed., *Catalysis*, Vol. VI (1958):

| Octane Numbers of Pure Hydrocarbons | |
|---|---|
| Hydrocarbon | Blending Research Octane Number (clear) |
| Paraffins: | |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

The feedstock for the present process is one which contains significant amounts of $C_5+$ normal and/or slightly branched paraffins. In addition, the feedstock contains monocyclic aromatic compounds and/or cyclic paraffins, such as cyclohexane. Among the hydrocarbons having 6 or less carbon atoms in the feedstock, at least 1 wt. %, e.g. at least 5 wt. %, e.g. at least 10 wt. %, e.g. at least 20 wt. %, e.g. at least 30 wt. %, of these hydrocarbons may be cyclic hydrocarbons, e.g. aromatics or cyclic paraffins.

The feedstream to the present first reaction zone is one where $C_7+$ hydrocarbons have been removed therefrom. A preferred separation technique for removing $C_7+$ hydrocarbons from this stream is by distillation, although other separation techniques, such as chromatography, are also possible. It will be understood, however, that such distillation separation is not always entirely effective in removing all $C_7$ hydrocarbons from the feedstream. In particular, certain lower boiling $C_7$ paraffins, such as highly branched heptanes, have boiling points very close to higher boiling $C_6$ hydrocarbons, such as cyclohexane and benzene. For example, the boiling points of the following hydrocarbons are listed in parentheses thereafter: cyclohexane (80.7° C.); benzene (80.1° C.); 2,4-dimethylpentane (80.5° C.); and 2,2,3-trimethylbutane (81.0° C.). Higher boiling $C_7$ hydrocarbons, such as singly branched or straight chain heptanes, are more easily separated from benzene and cyclohexane by distillation. For example, the boiling points of the following heptanes are given in parentheses thereafter: 2-methylhexane (90.0° C.); 3-methylhexane (92° C.); n-heptane (98.4° C.).

Accordingly, it will be understood that the feedstream to the present first reaction zone will contain, at most, only a small amount of $C_7$ hydrocarbons (e.g., less that 5 wt. %, possibly in the form of highly branched heptanes) and may contain even less of singly branched and normal heptanes (e.g., less than 2 wt. %). This feedstream will also contain, at most, only a very small amount of $C_8+$ hydrocarbons (e.g., less than 2 wt. %). The present reaction zone is, therefore, quite distinct from reformer feedstreams, which include substantial amounts of $C_7+$ hydrocarbons including substantial amounts of $C_8+$ hydrocarbons.

The catalyst composition employed in the first reaction zone comprises a dehydrogenation/hydrogenation metal and a zeolite.

The zeolite is to be used in intimate combination with a dehydrogenation/hydrogenation component such as tungsten, vanadium, molybdenum, rhenium, nickel, cobalt, chromium, manganese, or a noble metal such as platinum, palladium or iridium. Such component can be introduced in the catalyst composition to the extent a Group IIIA element, e.g. aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex. The amount of the dehydrogenation/hydrogenation component in the catalyst composition can range from 0.01 to 20 weight percent of the composition.

A convenient measure of the extent to which a zeolite provides control of access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size, e.g. greater than 7 Angstroms. The method by which Constraint Index is determined is described fully in U.S. Pat. No. 4,016,218, incorporated herein by reference for details of the method.

The zeolite of the first reaction zone may be a medium or large pore size zeolite. This zeolite may have a Constraint Index of 12 or less. Zeolites having a Constraint Index of 2-12 are generally regarded to be medium pore size zeolites. Zeolites having a Constraint Index of less than 1 are generally regarded to be large pore size zeolites. Zeolites having a Constraint Index of 1-2 may be regarded as either medium or large pore size zeolites.

The members of the class of medium pore size zeolites may have an effective pore size of generally from about 5 to about 8 Angstroms, such as to freely sorb normal hexane. In addition, the structures provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the medium pore size type. Windows of 10-membered rings are preferred, although, in some instances, excessive puckering of the rings or pore blockage may render these zeolites ineffective.

Although 12-membered rings in theory would not offer sufficient constraint to constitute a medium size pore, it is noted that the puckered 12-ring structure of TMA offretite does show some constrained access. Other 12-ring structures may exist which may be regarded to be medium pore sized, and therefore, it is not the present intention to classify a particular zeolite solely from theoretical structural considerations.

Constraint Index (CI) values for some typical materials are:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Mordenite | 0.5 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y (Deal Y) | 0.5 (510° C.) |
| Erionite | 38 (316° C.) |
| Zeolite Beta | 0.6–2.0 (316° C.–399° C.) |

The above-described Constraint Index provides a definition of those zeolites which are particularly useful in the present process. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein of 12 or less.

Examples of zeolites having a Constraint Index of from 1 to 12 include ZSM-5, ZSM-11, ZSM-12, ZSM-22, ZSM-23, ZSM-35, ZSM-38 and ZSM-48.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in greater detail in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. Pat. No. 4,556,477, the entire contents of which is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,406,859. The description of that zeolite, and particularly the specified X-ray diffraction pattern thereof, is incorporated herein by reference.

ZSM-48 is more particularly described in U.S. Pat. No. 4,234,231, the entire contents of which is incorporated herein by reference.

The large pore zeolites, including those zeolites having a Constraint Index less than 2, are well known to the art and have a pore size sufficiently large to admit the vast majority of components normally found in a feed chargestock. The zeolites are generally stated to have a pore size in excess of 7 Angstroms and are represented by zeolites having the structure of, e.g. Zeolite Beta, Zeolite Y, Ultrastable Y (USY), Dealuminized Y (Deal Y), Mordenite, ZSM-3, ZSM-4, ZSM-18 and ZSM-20. A crystalline silicate zeolite well known in the art and useful in the present invention is faujasite. The ZSM-20 zeolite resembles faujasite in certain aspects of structure, but has a notably higher silica/alumina ratio than faujasite, as does Deal Y.

Although Zeolite Beta has a Constraint Index less than 2, it is to be noted that it does not have the same structure as the other large pore zeolites, nor does it behave exactly like a large pore zeolite. However, Zeolite Beta is a particularly preferred zeolite for use in the present first reaction zone.

Zeolite ZSM-4 is described in U.S. Pat. No. 3,923,639, to which reference is made for details of this catalyst.

Zeolite ZSM-20 is described in U.S. Pat. No. 3,972,983, to which reference is made for details of this catalyst.

Zeolite Beta is described in U.S. Pat. Nos. 3,308,069, and Re. 28,341, to which reference is made for details of this catalyst.

Low sodium Ultrastable Y molecular sieve (USY) is described in U.S. Pat. Nos. 3,293,192 and 3,449,070, to which reference is made for details of this catalyst.

Dealuminized Y zeolite (Deal Y) may be prepared by the method found in U.S. Pat. No. 3,442,795, to which reference is made for details of this catalyst.

Zeolite UHP-Y is described in U.S. Pat. No. 4,401,556, to which reference is made for details of this catalyst.

Another zeolite which may be used in the present first reaction zone is MCM-22. MCM-22 is described in U.S. Pat. No. 4,954,325, as well as in U.S. Pat. No. 5,107,054, the entire disclosures of which are expressly incorporated herein by reference.

Zeolites with intersecting pore systems, such as Zeolite Beta and Zeolite Y, are of particular interest in the present process.

The zeolite crystals can be shaped into a wide variety of particle forms. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite with another material which is resistant to the temperatures and other conditions employed in the present process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e. combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In the first reaction zone, the temperature should be high enough to promote substantial ring opening without causing excessive cracking of hydrocarbons to $C_4-$ hydrocarbons. This reaction temperature may be at least 150° C., e.g. from 230° C. to 270° C. Pressures range from atmospheric up to 1000 psig. The preferred range is from 50 to 500 psig. Weight hourly space velocity is generally from 0.1 to 50 $hr^{-1}$, more usually 0.2 to 10 $hr^{-1}$. The hydrogen:hydrocarbon molar ratio in the charge stock to the first reaction zone is generally from 0.1:1 to 10:1.

The reaction conditions in the first reaction zone may be sufficient to cause at least 10 wt. %, e.g. at least 25 wt. %, e.g. at least 50 wt %, of the cyclic hydrocarbons introduced into this zone to undergo ring opening.

The feedstream to the present second reaction zone will have essentially the same small $C_{7}+$ hydrocarbon content as the feedstream to the present first reaction zone. In particular, the feedstream to the second reaction zone may have less than 5 wt. % of $C_7$ hydrocarbons and less than 2 wt. % of $C_8+$ hydrocarbons. Thus, the feedstream to the second reaction zone is quite different from feedstreams to reformers.

The reaction conditions in the present second reaction zone are also quite different from those employed in reformers, particularly in terms of temperature. The temperatures employed in reformers are usually greater than 800° F. (427° C.). On the other hand, the temperature in the present second reaction zone may be less than 650° F. (343° C.), preferably less than 518° F. (270° C.), even when relatively less active isomerization catalysts are used. When more highly active isomerization catalysts, as discussed hereinbelow, are used, the temperature in the second reaction zone may be 180° C. or less.

The reaction conditions in the second reaction zone may be milder than the conditions in the first reaction zone, particularly in terms of lower temperature conditions, to optimize isomerization of paraffins to higher octane value isomers. The theoretical equilibrium concentration of high octane isomers, such as 2,2-dimethylbutane, increases with lower temperature conditions. Thus, high yields of desirable high octane isomers are achievable at lower temperature conditions.

In order to use lower temperatures in the second reaction zone, one may use a catalyst which is more active for isomerization than the zeolite-containing catalyst used in the first reaction zone. Examples of such more reactive catalysts, which may be used in the second reaction zone, include those catalysts described in U.S. Pat. Nos. 4,783,575; 4,804,803; and 4,834,866, the entire disclosures of which are expressly incorporated herein by reference. These catalysts comprise alumina, platinum and a chloride component.

The isomerization catalyst in the second reaction zone may be a high chloride catalyst on an aluminum base containing platinum. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst may contain at least about 0.1 wt. %, e.g. from about 0.1 to about 1.0 wt. %, e.g. from about 0.1 to 0.25 wt. %, of platinum. Other platinum group metals may be present in a concentration of at least about 0.1 wt. %, e.g. from about 0.1 to 1.0 wt. %, e.g. from 0.1 to 0.25 wt. %. The platinum component may exist within the final catalytic composite as an oxide or halide or as an elemental metal. The presence of the platinum component in its reduced state has been found most suitable for this process.

The catalyst of the second reaction zone may also contain a chloride component. The chloride component termed in the art "a combined chloride" may be present in an amount of at least about 2 wt. %, e.g. from about 2 to about 20 wt. %, e.g. from about 2 to about 10 wt. %, based upon the dry support material. The use of chloride in amounts greater than 5 wt. % have been found to be the most beneficial for this process.

There are a variety of ways for preparing this catalytic composite and incorporating the platinum metal and the chloride therein. One method prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the chloride concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the feedstock contacting this catalyst must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

It has been recognized that cyclic hydrocarbons, especially $C_6$ cyclics such as benzene, cyclohexane and methylcyclopentane adversely affect the degree of paraffin isomerization over this particular type of alumina/platinum/chloride catalyst. The adverse effect is believed to be caused by preferential adsorption of the cyclic hydrocarbons on the catalyst surface and the resulting exclusion of the paraffinic hydrocarbons. However, the adverse effect is minimized by substantially removing cyclics in the first reaction zone. Operating conditions within the second reaction zone are selected to maximize the production of isoalkane product from the feed components. Temperatures within the reaction zone will usually range from about 40° C. to 180° C. Lower reaction temperatures are preferred for purposes of isomerization conversion since they favor isoalkanes over normal alkanes in equilibrium mixtures.

The hydrogen to hydrocarbon molar ratio in the second reaction zone may be from 0.01 to 10, e.g. from 0.01 to 5. However, it is noted that the primary reaction, i.e. isomerization, which takes place in this zone, does not consume net hydrogen. Furthermore, the types of side reactions, e.g. saturation of olefins and aromatics, which consume hydrogen, take place primarily in the first reaction zone. Accordingly, the hydrogen to hydrocarbon molar ratio in the second reaction zone may be quite small, e.g. 0.05 or less.

The pressure in the second reaction zone may be maintained over a wide range of pressures. Pressure conditions range from 50 to 1500 psig. The feed rate to the second reaction zone can also vary over a wide range. These conditions include weight hourly space velocities ranging from 0.1 to 50 hr.$^{-1}$, however, space velocities between 0.5 and 3 hr.$^{-1}$ are preferred.

When the above-mentioned alumina/platinum/chloride catalyst is used, operation of the second reaction zone also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

More than one reactor may be employed in each of the above-mentioned reaction zones. The use of two reactors permits a variation in the operating conditions between the two reactors to enhance cyclic hydrocarbon conversion in the first reactor. In this manner, the first reactor operates at higher temperature and pressure conditions that favor ring opening. The likelihood of exothermic reactions, such as the hydrogenation of unsaturates, occurring in the initial portion of the reaction zone facilitates the use of higher temperatures therein. Once the rings have been opened, the final reactor stage may operate at temperature conditions that are more favorable for isoalkane equilibrium.

Another benefit of using two reactors is that it allows partial replacement of the catalyst system without taking the isomerization unit off stream. For short periods of time, during which the replacement of catalyst may be necessary, the entire flow of reactants may be processed through only one reaction vessel while catalyst is replaced in the other.

After the feedstock has encountered the second reaction zone, the effluent of the process will enter separation facilities in the recovery of an isoalkane product. At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal isoalkanes. Normal isoalkanes recovered from the separation facilities may be recycled to the isomerization reaction zone to increase the conversion of normal alkanes to isoalkanes. Typical separation facilities will comprise a stabilizer section that receives the effluent from the reaction and includes at least one stabilizer column. The stabilizer column is operated to deliver a bottoms fraction containing $C_4$ and heavier hydrocarbons and an overhead fraction of $C_3$ hydrocarbons and lighter boiling compounds. The heavier hydrocarbons recovered from the bottom of the stabilizer column are cooled and may be further separated into a product stream and a reflux stream. $C_3$ and lighter hydrocarbons taken overhead from the stabilizer column are cooled, condensed and separated into a reflux stream that is returned to the process and a wet gas stream. The wet gas stream enters a scrubber section that contacts the gas with a suitable treatment solution for neutralizing and/or removing acidic components that may have originated with the chloride addition to the isomerization zone and may by present in the gas stream.

FIG. 1 provides a schematic representation of an embodiment of the present process $C_6+$ naphtha enters through line 10 to distillation column 12. The $C_6+$ naphtha is separated into three fractions: high octane $C_6$ isoparaffins (primarily 2,2-dimethylbutane) which are collected overhead in line 14 and used as a high octane blending component; lower octane $C_6$ paraffins (i.e. 2-methylpentane) and cycloparaffins (i.e. cyclohexane) which are concentrated in line 16; and $C_7+$ hydrocarbons which are sent via line 18 to the reformer.

Low octane $C_6$ paraffins and cycloparaffins are piped from distillation column 12 via line 16 to reactor 20. The $C_6$ cut is mixed with hydrogen stream 56 prior to entering reactor 20. The molar ratio of hydrogen to hydrocarbon in the mixed feed can range from about 5/1 to 0.01/1. Reactor 20 contains a high activity, noble metal containing zeolite. Reactor 20 pressure can range from 50–1500 psig, preferably about 450 psig. $C_6+$ feed rates can vary from about 0.1 to 10 LHSV. The low octane paraffins and cycloparaffins in the $C_6$ cut are partially converted to isoparaffins in Reactor 20. The effluent from Reactor 20 passes through heat exchanger 22 via line 24, and into an isomerization reactor 40 via line 25.

Reactor 40 contains an amorphous, chlorided alumina catalyst. Reactor 40 pressure can range from 50–1500 psig, preferably about 435 psig. Feed rates can vary from about 0.1 to 10 LHSV. A small amount of organic chloride (10–500 ppm Cl on total feed) is injected into the feed prior to reactor 40. Organic chlorides, such as carbon tetrachloride, are needed to maintain isomerization activity of chlorided alumina catalysts. The total effluent from reactor 40 is passed to liquid-gas separator 50 via line 42. Gas in the separator is mixed with makeup hydrogen from line 52 and recycled via line 55 through compressor 54 and line 56 to reactor 20. Recycle gas is a mixture of $C_4-$ hydrocarbons, hydrogen and chloride promoter.

$C_6$ paraffins and cycloparaffins are partially converted to isoparaffins in Reactor 40. The liquid component in the gas-liquid separator is sent via line 58 to distillation column 60. $C_5+$ hydrocarbons are collected from the bottom of the column and recycled via line 62 to distillation column 12 where high octane isoparaffins are collected overhead in line 14 and used as a high octane blending component. Unconverted $C_6$ paraffins and cycloparaffins are reacted to extinction by recycling through line 16. Normally gaseous compounds which are soluble in the liquid from the gas-liquid separator 50 ($H_2$, chloride promoter, $C_4-$ hydrocarbons) are concentrated at the top of distillation of column 60 and piped to a caustic scrubber and/or isobutane recovery facility via line 64.

A $C_5$ paraffin stream may be upgraded with this process. The $C_5$ paraffin stream may enter the process prior to reactor 20 and reactor 40.

Figure 2:
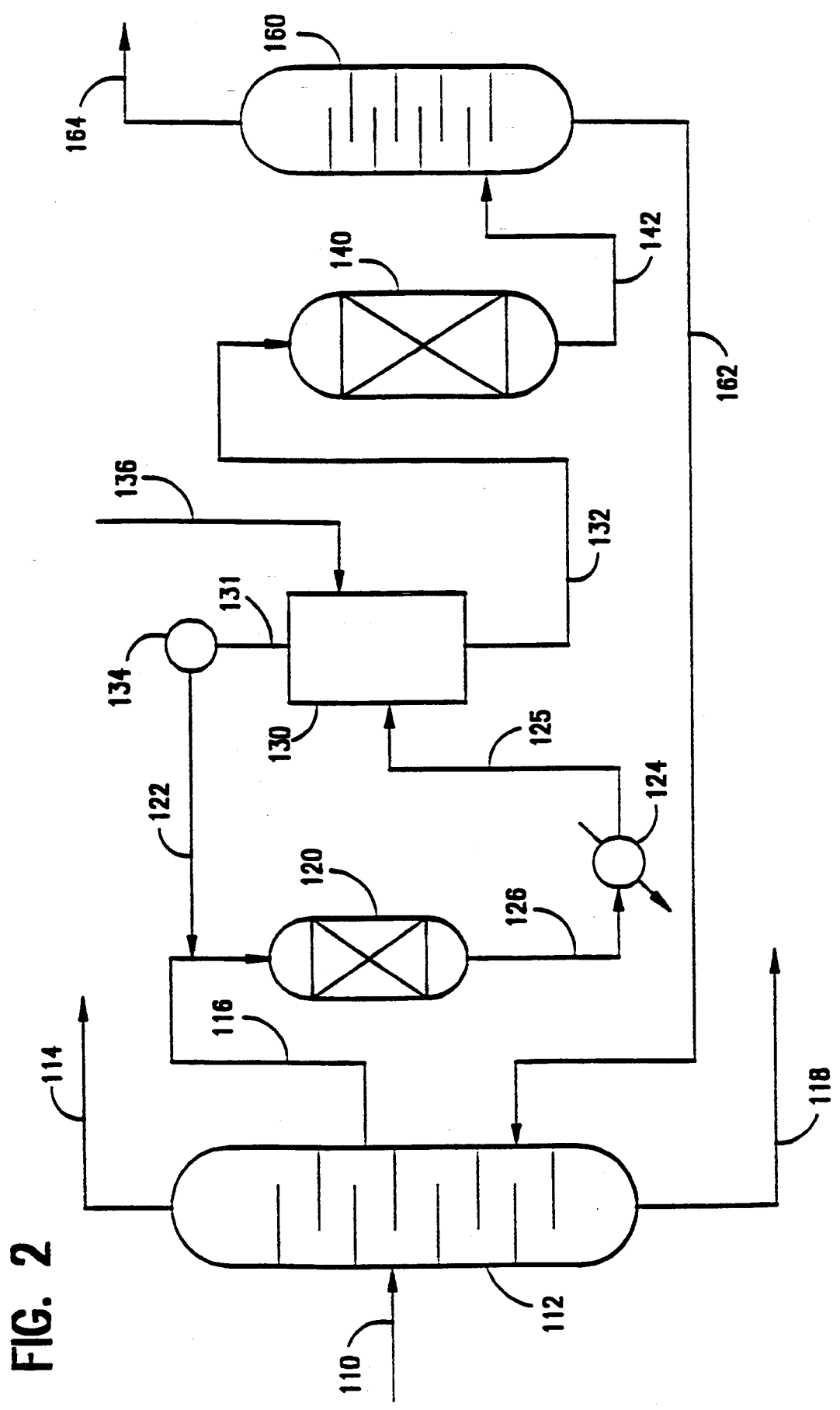

FIG. 2 provides a schematic representation of another embodiment of the present process.

$C_6+$ naphtha enters through line 110 into distillation column 112. The distillation column produces three cuts: a high octane blending fraction termed "isomerate" (primarily 2,2-dimethylbutane and lighter hydrocarbons) which is piped overhead via line 114 to the refinery gasoline pool, a $C_7+$ fraction piped from the bottom through line 118 to the reformer, and a $C_6$ hydrocarbon fraction which passes through line 116 to Reactor 120. The $C_6$ hydrocarbon fraction contains hexane, methylpentanes, 2,3-dimethylbutane, methylcyclopentane and cyclohexane as the predominant components.

The low octane $C_6$ paraffins and cycloparaffins are piped from distillation column 112 via line 116 to Reactor 120. The $C_6$ cut is mixed with hydrogen stream in line 122 prior to entering Reactor 120. The molar ratio of hydrogen to hydrocarbon in the mixed feed can range from about 5/1 to 0.01/1. Reactor 120 contains a high activity, noble metal loaded zeolite. Reactor 120 pressure can range from 50–1500 psig, preferably about 450 psig. $C_6$ feed rates to Reactor 120 can vary from about 0.1 to 10 LHSV. The low octane paraffins and cycloparaffins in the $C_6$ cut are partially converted to isoparaffins in Reactor 120. The effluent from Reactor 120 passes through heat exchanger 124 from line 126, and into gas-liquid separator 130 via line 125.

The liquid component from gas-liquid separator 130 passes to Reactor 140 via line 132. The feed to Reactor 140 contains only dissolved hydrogen, no make-up hydrogen is added. The gaseous component from gas-liquid separator 130 is recycled via line 131 through compressor 134 and via line 122 to Reactor 120. The recycle gas contains mostly hydrogen with a lesser amount of $C_4-$ hydrocarbons. Pure hydrogen can be added to the separator via line 136 to adjust the hydrogen purity in stream 122.

Reactor 140 contains an amorphous, chlorided alumina catalyst. Reactor 140 pressure can range from 50–1500 psig, preferably about 435 psig. Feed rates can vary from about 0.1 to 10 LHSV. A small amount of organic chloride (10–500 ppm Cl on total feed) is injected into the feed prior to Reactor 140. Organic chlorides, such as carbon tetrachloride, are needed to maintain isomerization activity of chlorided alumina catalysts.

$C_6$ paraffins and cycloparaffins are partially converted to isoparaffins in Reactor 140. The total effluent from Reactor 140 passes through line 142 to distillation column 160. $C_5+$ hydrocarbons are collected from the bottom of distillation column 160 and recycled via line 162 to distillation column 112 where high octane isomerate is collected overhead and low octane $C_6$ paraffins and cycloparaffins are reacted to extinction by recycling through line 116. Normally gaseous products which are soluble in the effluent from Reactor 140 ($H_2$, chloride promoter, $C_4-$ hydrocarbons) are concentrated at the top of distillation column 160 and piped to a caustic scrubber and/or isobutane recovery facility via line 164.

A $C_5$ paraffin stream may also be upgraded with this process. The $C_5$ paraffin stream may enter the process prior to Reactor 120 or Reactor 140.

EXAMPLE 1

USY was exchanged with an aqueous solution of $Pt(NH_3)_4Cl_2$. The exchanged USY was collected by filtration, washed twice with deionized water, and dried at 250° F. for 16 hrs. The dried catalyst was calcined for 10 hrs in air at 660° F. Catalyst properties are given in Table 1.

TABLE 1

| Pt/USY Catalyst Properties | |
|---|---|
| Platinum, wt % | 1.2 |
| Sodium, ppm | 1070 |
| Ash Content, wt % | 91.1 |
| Surface Area, m²/g | 610 |

EXAMPLE 2

A platinum Zeolite Beta containing catalyst was prepared by calcining a 65%/35% alumina extrudate for 3 hours in nitrogen at 900° F. followed by 3 hours in air at 1000° F. The calcined extrudate was exchanged for 4 hours at room temperature with a 6.62 mM solution of $Pt(NH_3)_4Cl_2$ in 1.0N $NH_4NO_3$. A pH of 9 was maintained throughout the exchange by addition of 1N $NH_4OH$. The catalyst was filtered and washed with deionized water until chloride free. The exchanged material was dried at 250° F. and calcined for 3 hours in air at 660° F. The final catalyst contained 0.50 wt % platinum.

EXAMPLE 3

The platinum impregnated zeolites described in Examples 1 and 2 were tested for $C_6$ hydrocarbon ring opening in a microunit equipped with a ½ downflow stainless steel reactor. In a typical experiment, 10 cc of sized catalyst (14/24 mesh) were loaded into the reactor and reduced in hydrogen at 800° F. for 2 hours with hydrogen. A hydrocarbon feed with the composition shown in Table 2 was introduced at a rate of 4 vol/vol catalyst/hr with a 2/1 mole/mole $H_2/HC$ co-feed. The product from the reactor was analyzed with an on-line gas chromatograph equipped with a 30 meter megabore DB-1 column.

TABLE 2

| Model Feed Composition | |
|---|---|
| Component | Wt % |
| n-hexane | 42.1 |
| 2-methylpentane | 0.9 |
| 3-methylpentane | 1.3 |
| 2,3-dimethylbutane | 0.1 |
| cyclopentane | 0.1 |
| cyclohexane | 35.3 |
| methylcyclopentane | 16.4 |
| benzene | 3.8 |
| t-butyl chloride | 20 ppm |

Figure 3:
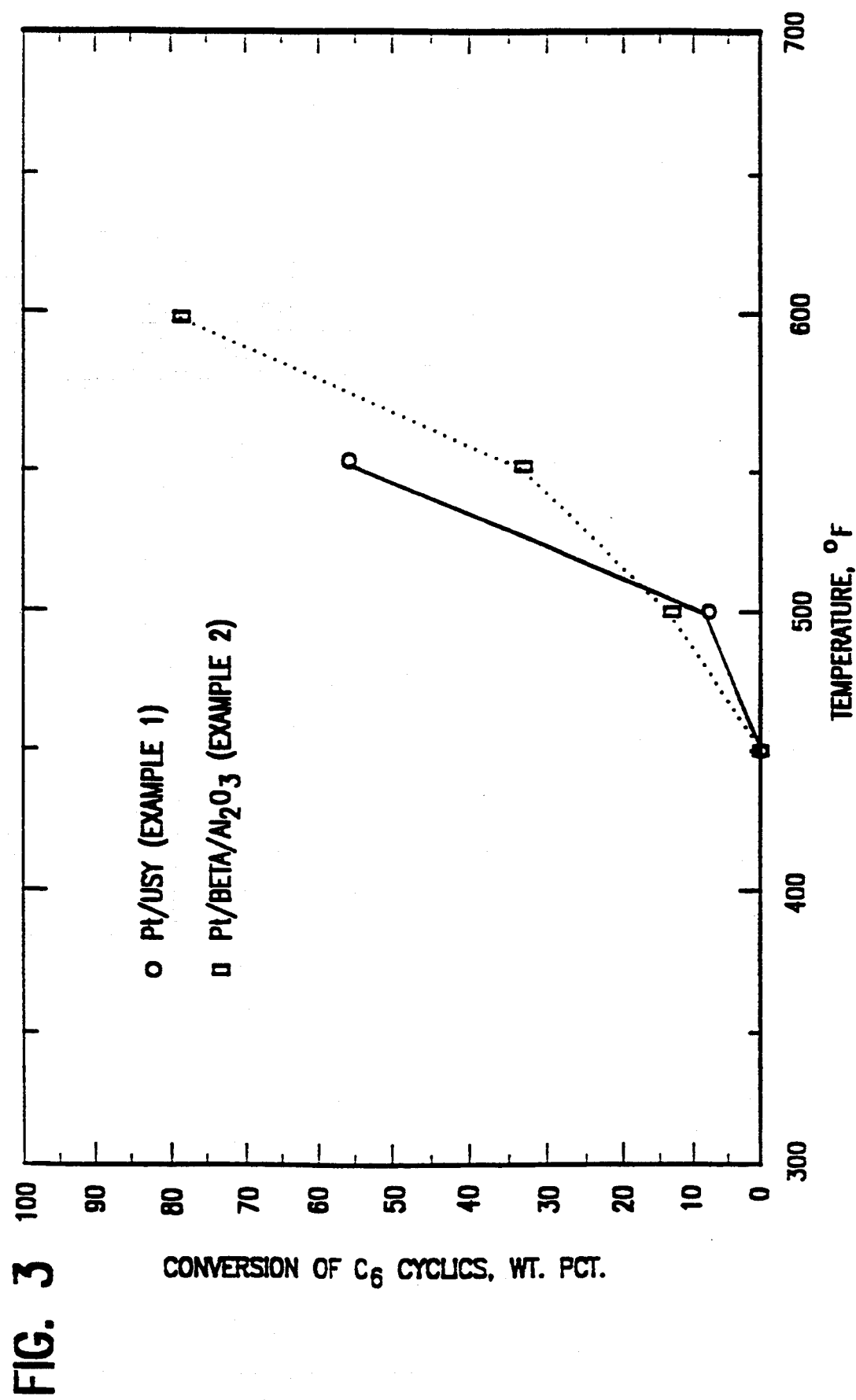
FIG. 3 provides a graph plotting conversion of $C_6$ cyclics vs. temperature.
Figures 4A, 4B:
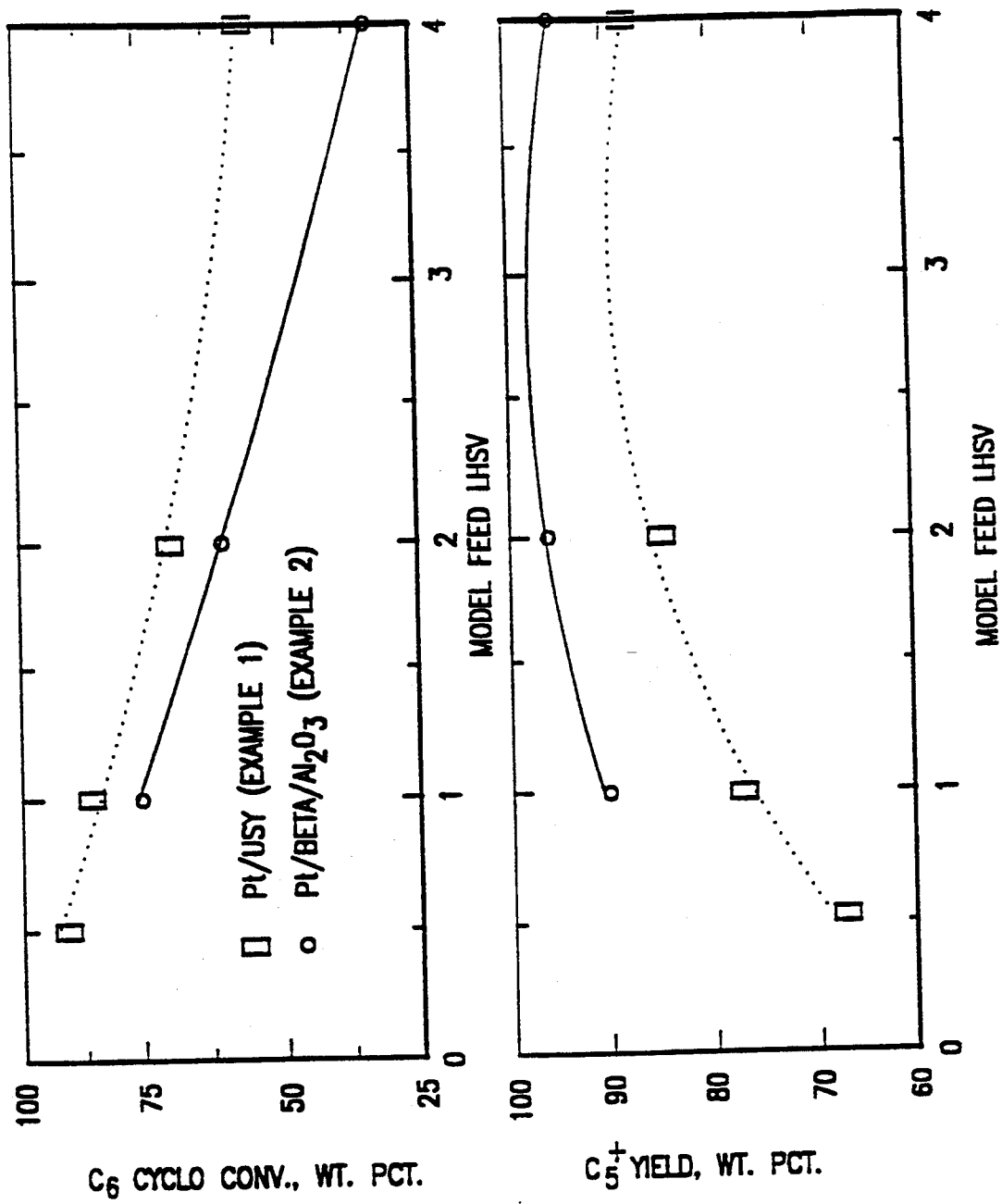
FIGS. 4A and 4B provide two graphs. One graph (FIG. 4A) plots $C_6$ cyclics conversion vs. feed LHSV, and the other graph (FIG. 4B) plots $C_5+$ yield vs. feed LSHV.

FIG. 3 shows conversion of $C_6$ cyclics in the model feed as a function of temperature for both Pt/USY and Pt/Beta/$Al_2O_3$ catalysts. At 435 psig and 4 LHSV, the zeolite catalysts showed appreciable ring opening activity (>10%) at temperatures above 500° F. FIGS. 4A and 4B display conversion of $C_6$ cyclics and $C_5+$ yield as a function of feed rate. Conversion of $C_6$ cyclics in the model feed increased at lower feed rates. For instance, conversion of $C_6$ cyclics at 550° F. with Pt/USY was approximately 55% at 4 LHSV and 95% at 0.5 LHSV. Yield of $C_5+$ product decreased at lower feed rates. However, Pt/Beta/$Al_2O_3$ still afforded 90+% $C_5+$ yield at 80% conversion of $C_6$ cyclics. Table 3 gives product compositions for both catalysts at 550° F. and 1 LHSV. The $C_4-$ product in each case contains predominantly isobutane which can be upgraded to alkylate or MTBE.

TABLE 3

| COMPARISON OF EXAMPLE 1 AND EXAMPLE 2 CATALYSTS AT 550° F. AND 1 LHSV | | |
|---|---|---|
| Product Compositions, wt. % | Example 1 Pt/USY | Example 2 Pt/Beta/$Al_2O_3$ |
| $C_1$ & $C_2$, wt % | 0.04 | 0.00 |
| $C_3$ | 3.44 | 1.17 |
| n-$C_4$ | 3.36 | 1.56 |
| iso-$C_4$ | 16.72 | 6.58 |
| n-$C_5$ | 5.68 | 2.91 |
| iso-$C_5$ | 12.47 | 5.92 |
| Cyclopentane | 1.12 | 1.70 |
| n-$C_6$ | 9.57 | 13.35 |
| iso-$C_6$ | 38.21 | 53.48 |
| Methylcyclopentane | 4.20 | 8.50 |
| Cyclohexane | 1.13 | 2.00 |
| $C_7+$ | 4.06 | 2.83 |

What is claimed is:

1. A process for ring opening and isomerization of hydrocarbons, wherein cyclohexane and lower octane $C_6$ paraffins are converted to high octane $C_6$ paraffins comprising 2,2-dimethylbutane, said process comprising the steps of:

(a) charging hydrocarbons having 6 or less carbon atoms comprising at least 10 wt. % $C_6$ cyclic hydrocarbons along with hydrogen to a first reactor, wherein said hydrocarbons and hydrogen are contacted with a catalyst comprising an aluminosilicate zeolite, wherein said zeolite is Zeolite Y or Zeolite Beta, and a hydrogenation component under conditions sufficient to saturate benzene and open cyclic hydrocarbons contained in said hydrocarbons, wherein cyclohexane is converted to branched paraffins, wherein $C_{7+}$ hydrocarbons have been removed from the hydrocarbons which are charged to said first reactor, and wherein the hydrocarbons which are charged to said first reactor comprise less than 5 wt. % of $C_7$ hydrocarbons and less than 2 wt. % of $C_8$ hydrocarbons; and (b) charging the hydrocarbon product from said first reactor along with hydrogen to a second reactor, wherein hydrocarbons and hydrogen are contacted with an isomerization catalyst under conditions sufficient to isomerize paraffins, wherein the temperature in said second reactor is less than 343° C., and wherein lower octane $C_6$ paraffins are converted to high octane $C_6$ isoparaffins comprising 2,2-dimethylbutane.

2. A process according to claim 1, wherein said zeolite is Zeolite Beta.

3. A process according to claim 1, wherein the reaction conditions in the first reactor include a temperature of at least 150° C., a pressure of from 50 to 1500 psig and a weight hourly space velocity of from 0.1 to 50 $hr^{-1}$.

4. A process according to claim 3, wherein the reaction conditions in the second reactor include a temperature of from about 40° to 180° C., a pressure of from 50 to 1500 psig and a weight hourly space velocity of from 0.1 to 50 $hr^{-1}$.

5. A process according to claim 1, wherein at least 10 wt. % of the cyclic hydrocarbon rings charged into said first reactor are opened in step (a).

6. A process according to claim 1, wherein the hydrocarbons which are charged to said second reactor comprise less than 5 wt. % of $C_7$ hydrocarbons and less than 2 wt. % of $C_8$ hydrocarbons.

7. A process according to claim 6, wherein the temperature in said second reactor is less than 270° C.

8. A process for ring opening and isomerization of hydrocarbons, wherein cyclohexane and lower octane $C_6$ paraffins are converted to high octane $C_6$ paraffins comprising 2,2-dimethylbutane, said process comprising the steps of:

(a) passing hydrocarbons having 6 or less carbon atoms comprising at least 10 wt. % $C_6$ cyclic hydrocarbons and a hydrocarbon recycle stream to a fractionation zone, wherein said cyclic hydrocarbons comprise cyclohexane;

(b) withdrawing a sidecut comprising $C_6$ hydrocarbons and a majority of the $C_6$ cyclic hydrocarbons entering said fractionation zone;

(c) charging said sidecut along with hydrogen to a first reactor, wherein said sidecut and hydrogen are contacted with a catalyst comprising an aluminosilicate zeolite, wherein said zeolite is Zeolite Y or Zeolite Beta, and a hydrogenation component under conditions sufficient to saturate benzene and open cyclic hydrocarbons contained in the sidecut, wherein cyclohexane is converted to branched paraffins;

(d) charging the hydrocarbon product from said first reactor along with hydrogen to a second reactor, wherein hydrocarbons and hydrogen are contacted with an isomerization catalyst under conditions sufficient to isomerize paraffins, wherein the temperature in said second reactor is less than 343° C., and wherein lower octane $C_6$ paraffins are converted to high octane $C_6$ isoparaffins comprising 2,2-dimethylbutane;

(e) recovering an effluent from said second reactor and returning said effluent to said fractionation zone as said hydrocarbon recycle stream;

(f) recovering a second stream from said fractionation zone comprising $C_7$ hydrocarbons; and (g) recovering a third stream from said fractionation zone comprising 2,2-dimethylbutane and lower boiling hydrocarbons.

9. A process according to claim 8 wherein said zeolite is Zeolite Beta.

10. A process according to claim 8, wherein said catalyst in the first reactor and the catalyst in the second reactor each comprise platinum.

11. A process according to claim 8 wherein $C_5$ hydrocarbons are cofed into the reactor of step (c).

12. A process according to claim 8, wherein at least 25 wt. % of the cyclic hydrocarbon rings charged into said first reactor are opened in step (c).

13. A process according to claim 8, wherein the hydrocarbons which are charged to said first reactor comprise less than 5 wt. % of $C_7$ hydrocarbons and less than 2 wt. % of $C_{8+}$ hydrocarbons.

14. A process according to claim 13, wherein the hydrocarbons which are charged to said second reactor comprise less than 5 wt. % of $C_7$ hydrocarbons and less than 2 wt. % of $C_8$ hydrocarbons.

15. A process according to claim 14, wherein the temperature in said second reactor is less than 270° C.

16. A process for ring opening and isomerization of hydrocarbons, wherein cyclohexane and lower octane $C_6$ paraffins are converted to high octane $C_6$ paraffins comprising 2,2-dimethylbutane, said process comprising the steps of:

(a) passing hydrocarbons having 6 or less carbon atoms comprising at least 10 wt. % $C_6$ cyclic hydrocarbons and a hydrocarbon recycle stream to a fractionation zone, wherein said cyclic hydrocarbons comprise cyclohexane;

(b) withdrawing a sidecut comprising $C_6$ hydrocarbons and a majority of the $C_6$ cyclic hydrocarbons entering said fractionation zone;

(c) charging said sidecut along with hydrogen to a first reactor, wherein said sidecut and hydrogen are contacted with a catalyst comprising an aluminosilicate zeolite, wherein said zeolite is Zeolite Y or Zeolite Beta, and a hydrogenation component under conditions sufficient to saturate benzene and open cyclic hydrocarbons contained in the sidecut, wherein cyclohexane is converted to branched paraffins;

(d) removing hydrogen from the effluent of the first reactor under conditions so that the effluent has a hydrogen to hydrocarbon mole ratio of less than 0.05;

(e) recycling hydrogen removed in accordance with step (d) to said first reactor;

(f) charging the effluent from said first reactor having a hydrogen to hydrocarbon mole ratio of less than 0.05 to a second reactor, wherein hydrocarbons and hydrogen are contacted with an isomerization catalyst under conditions sufficient to isomerize paraffins, wherein the temperature in said second reactor is less than 343° C., and wherein lower octane $C_6$ paraffins are converted to high octane $C_6$ isoparaffins comprising 2,2-dimethylbutane;

(g) recovering an effluent from said second reactor and returning said effluent to said fractionation zone as said hydrocarbon recycle stream;

(h) recovering a second stream from said fractionation zone comprising $C_7$ hydrocarbons; and (i) recovering a third stream from said fractionation zone comprising 2,2-dimethylbutane and lower boiling hydrocarbons.

17. A process according to claim 16, wherein said zeolite is Zeolite Beta.

18. A process according to claim 16, wherein the catalyst in the second reactor comprises alumina, from 0.1 to 1.0 wt. % platinum, and from 2 to 20 wt % of a chloride component.

19. A process according to claim 18, wherein a chloride concentration of from 30 to 300 ppm is maintained in said second reactor.

20. A process according to claim 16, wherein at least 50 wt. % of the cyclic hydrocarbon rings charged into said first reactor are opened in step (c).

21. A process according to claim 16, wherein the hydrocarbons which are charged to said first reactor comprise less than 5 wt. % of $C_7$ hydrocarbons and less than 2 wt. % of $C_{8+}$ hydrocarbons.

22. A process according to claim 21, wherein the hydrocarbons which are charged to said second reactor comprise less than 5 wt. % of $C_7$ hydrocarbons and less than 2 wt. % of $C_8$ hydrocarbons.

23. A process according to claim 22, wherein the temperature in said second reactor is less than 270° C.

* * * * *